(12) United States Patent
Lawrentschuk

(10) Patent No.: US 8,033,283 B2
(45) Date of Patent: Oct. 11, 2011

(54) UROLOGY DRAPE

(75) Inventor: Nathan Lawrentschuk, Toronto (CA)

(73) Assignee: Urotech Pty Ltd, Sandringham (AU)

( * ) Notice: Subject to any disclaimer, the term of this patent is extended or adjusted under 35 U.S.C. 154(b) by 359 days.

(21) Appl. No.: 12/085,803

(22) PCT Filed: Nov. 21, 2006

(86) PCT No.: PCT/AU2006/001761
§ 371 (c)(1),
(2), (4) Date: Feb. 19, 2009

(87) PCT Pub. No.: WO2007/062454
PCT Pub. Date: Jun. 7, 2007

(65) Prior Publication Data
US 2009/0211587 A1    Aug. 27, 2009

(30) Foreign Application Priority Data

Nov. 30, 2005 (AU) ............................... 2005906709
May 16, 2006 (AU) ............................... 2006902614

(51) Int. Cl.
*A61B 19/08* (2006.01)
(52) U.S. Cl. ...................... 128/853; 128/849; 128/855
(58) Field of Classification Search .......... 128/849–850, 128/853–856; 604/355–357, 317, 327, 332; 600/573, 576, 580; 297/182; 383/36, 42, 383/59, 61.4, 71–72, 82–84, 88; 220/521–523, 220/526, 200, 256.1
See application file for complete search history.

(56) References Cited

U.S. PATENT DOCUMENTS

| 1,597,556 | A | | 8/1926 | Townsend |
| 2,584,249 | A | * | 2/1952 | Belcher .......................... 604/332 |
| 3,452,750 | A | | 7/1969 | Blanford |
| 3,660,033 | A | * | 5/1972 | Schwartz ....................... 436/174 |
| 3,791,382 | A | | 2/1974 | Collins |
| 4,007,741 | A | * | 2/1977 | Waldrop et al. ................ 604/357 |
| 4,169,472 | A | | 10/1979 | Morris |

(Continued)

FOREIGN PATENT DOCUMENTS

CN      1688262 A      10/2005

(Continued)

OTHER PUBLICATIONS

International Search Report, International Application No. PCT/AU2006/001761 (Jan. 23, 2007).

(Continued)

*Primary Examiner* — Patricia Bianco
*Assistant Examiner* — Kari Petrik
(74) *Attorney, Agent, or Firm* — Edwards Angell Palmer & Dodge LLP; Jeffrey D. Hsi; Brian R. Landry

(57) ABSTRACT

A urology drape is disclosed which comprises a flexible sheet (12) which has a flexible hood (22) overlying part of the sheet (12) to form a repository (24) between the sheet (12) and the hood (22). The sheet (12) has a hole (18) to enable a procedure to be performed on a patient when the drape is located on the patient. Bodily fluid is able to flow from the hole down the sheet (12) into the repository (24) and when the procedure is finished, the drape can be folded or otherwise collapsed into a disposable package so that the drape and fluid can be disposed of in a hygienic manner.

20 Claims, 4 Drawing Sheets

U.S. PATENT DOCUMENTS

| | | | |
|---|---|---|---|
| 4,559,937 A | | 12/1985 | Vinson |
| 4,570,628 A | | 2/1986 | Neal |
| 4,598,458 A | | 7/1986 | McAllester |
| 4,616,642 A | | 10/1986 | Martin et al. |
| 4,890,628 A | * | 1/1990 | Jackson .................. 128/849 |
| 4,955,666 A | * | 9/1990 | Baker ........................... 297/182 |
| 5,002,069 A | | 3/1991 | Thompson et al. |
| 5,148,940 A | * | 9/1992 | Mendise .................. 229/117.35 |
| 5,287,860 A | * | 2/1994 | Owens ........................... 128/851 |
| 5,388,593 A | | 2/1995 | Thomalla |
| 5,445,165 A | | 8/1995 | Fenwick |
| 5,494,050 A | | 2/1996 | Reyes |
| 5,975,082 A | * | 11/1999 | Dowdy ........................... 128/849 |
| 6,179,819 B1 | | 1/2001 | Haswell |
| 6,213,124 B1 | | 4/2001 | Butterworth |
| 6,725,864 B2 | * | 4/2004 | Ewonce et al. ............... 128/849 |
| 7,955,292 B2 | * | 6/2011 | Leroy et al. ..................... 604/13 |
| 2002/0078964 A1 | | 6/2002 | Kovac et al. |

FOREIGN PATENT DOCUMENTS

| | | |
|---|---|---|
| WO | WO-2004/021912 A1 | 3/2004 |
| WO | 2004028388 A1 | 4/2004 |
| WO | WO-2004/105627 A1 | 12/2004 |

OTHER PUBLICATIONS

Written Opinion of the International Searching Authority, International Application No. PCT/AU2006/001761 (Jan. 23, 2007).

International Preliminary Report on Patentability, International Application No. PCT/AU2006/001761 (Mar. 3, 2008).

Communication, European Patent Application No. 06827979.3-2310 (Nov. 23, 2009).

Communication, European Patent Application No. 06827979.3-2310 (Apr. 26, 2010).

* cited by examiner

UROLOGY DRAPE

FIELD OF THE INVENTION

This invention relates to a urology drape for use with a patient when changing a urinary catheter, performing of a manual bladder washout or performing flexible cystoscopy.

BACKGROUND OF THE INVENTION

The changing of a urinary catheter, performing of a manual bladder washout and flexible cystoscopy is conducted with the patient normally on a patient bed, occasionally a trolley and rarely an operating table. Male patients are in the supine position, females supine but with legs bent and apart with ankles together (the so-called "frog-leg" position).

Current urology drapes are small and offer partial protection from bodily fluids such as urine and blood. Using current draping methods, the majority of patients after having a urinary catheter changed, a manual bladder washout performed or a flexible cystoscopy, end up lying in wet sheets, bedding and clothing from urine and often blood either from the urine (haematuria) or from a traumatic catheterization. The patient's skin is also often in contact with the blood and urine.

The doctor or nurse performing the procedure and the patient are exposed to infectious materials because they are not well contained by current draping methods. Also, whoever attends the patient and/or needs to move the patient and change clothes and/or bed linen (nurse, patient services or clinical assistants, doctor) is further exposed to infectious material. Furthermore, the floor around the patient's bed or trolley is often covered with urine and blood necessitating cleaning staff to clean this infectious material and it is not uncommon for the shoes/clothes of staff to become soiled in the process.

This exposes healthcare workers to blood-borne pathogens.

Currently, having a urinary catheter changed, a manual bladder washout performed or a flexible cystoscopy often necessitates unnecessary exposure to hazardous material, wastes staff time and valuable hospital resources (bed linen, patient gowns and clothing needing cleaning), and therefore provides the following disadvantages:

1) Occupational Health and Safety (OHS)

The healthcare profession globally is actively focused on reducing OHS risks, to save lives, increase staff productivity/utilization by reducing sickness/infection, cut insurance costs and minimize the potential threat of litigation. The current draping methods/products for catheter and related procedures expose healthcare workers to substantial risks regarding infectious materials in the work place.

2) Patient Safety/Risk of Infection

By exposing patients to infectious material, it increases the patient's risk of infection.

3) Diminishment of Hospital Resources/Increased Costs

The current draping methods reduce valuable hospital resources and ultimately increase the cost of providing healthcare. In particular:

the costs associated with current OHS risks (highlighted above)
the time taken by hospital staff attending to the cleanup of patients/beds
soiled/contaminated linen requiring laundering
soiled/contaminated patient clothes/gowns that need laundering.

SUMMARY OF THE INVENTION

The object of the invention is to provide a drape and treatment method which addresses the above problems.

The invention provides a urology drape comprising:
a sheet for draping over a patient, the sheet having a first end and a second end, a hole in the sheet between the first and the second end for exposing the genital region of a patient; and
a hood overlying part of the sheet between the hole and the second end and attached to the sheet to define a repository between the sheet and the hood for catching bodily fluids.

Thus, according to the invention, blood and urine can flow down the sheet and if the sheet is partly absorbing, can be absorbed into the sheet with any overflow after full absorption by the sheet being collected in the repository. Thus, the blood and urine does not generally contaminate the. patient, the patient's clothing nor the bed coverings or floor surrounding the patient. Thus, patient cleanup is much easier and safer and requires less time than in the past. This therefore improves occupational health and safety for healthcare workers by reducing the risk of exposure to infectious materials, reduces the risk of infection to patients through exposure to infectious materials, saves costs and hospital resources because it reduces the time taken by healthcare workers to change soiled beds, patient's bed clothes and clean dirty floors, reduces laundry costs for bed linen and patient clothes/gowns, has the ability to reduce occupational health and safety claims, and potential reduction in insurance premiums, as well as the reduction of downtime caused by sick workers, and the use of additional catheter packs or material drapes are not required to be opened during a difficult catheterization, as there is a capacity to move from one catheter to another catheter without re-preparing or re-dressing the patient.

Preferably the first end of the sheet is wider than the second end so the drape tapers from the first end to the second end.

In one embodiment, a dam can be provided between the opening and the hood so as to prevent backflow of fluid captured in the repository towards the second end of the sheet.

Preferably the drape includes ties for tying a used drape into a bundle for disposal.

In one embodiment of the invention the sheet and hood are formed from waterproof plastic material. However, in some embodiments, the sheet could include a layer of absorbent material for absorbing liquids.

The hood may be connected to the sheet by adhesive, heat welding, stitching or any other suitable liquid impervious connection of the hood to the sheet.

In one embodiment of the invention the drape has a wall extending about the periphery of the sheet between the first end and the hood.

Preferably the wall is integral and forms a continuation of the hood, and a work area is defined between the hood and the wall.

Preferably the hole is provided in the work area.

The hole may be surrounded by an absorbent pad.

In one embodiment a perforation extends from the hole to a periphery of the drape for facilitating tearing of the drape to remove the drape from a patient.

In one embodiment of the invention the hood takes up a generally inverted V-shape configuration.

Preferably the hood includes a fold line for forming the inverted V-shape configuration.

However, in other embodiments the shape may be defined by a reinforcing at the fold line or within the hood.

The invention also provides a method of performing a urology procedure, comprising:
dressing the patient with a drape having a repository for collection of bodily fluids;

performing the urology procedure so that bodily fluids discharged as a result of the procedure collect in the repository; and removing the drape from the patient.

Preferably the drape includes ties and the method further comprises folding the drape into the repository and tying the folded drape with the ties for disposal of the used drape.

Preferably the method further comprises tilting the patient to facilitate flow of discharged liquid down into the repository.

In one embodiment, disposable articles used in the course of the procedure can also be located in the repository and disposed of with the drape.

Such articles may include swabs, gloves worn by the healthcare worker, and the like.

Preferably the drape is configured in the manner described above.

The invention also provides a urology drape comprising:
a flexible sheet for location on a patient between a patient's legs when the patient is in a supine position, the sheet having a first end and a second end;
a hole in the sheet at a first intermediate location between the first and second ends;
a flexible hood overlying the sheet and extending between the second end of the sheet and a second intermediate location between the second end and the first intermediate location;
the hood being connected to the sheet about the periphery of the hood except for an edge of the hood facing the hole;
the sheet and the hood forming a flexible repository therebetween for catching and retaining the bodily fluids; and
wherein after use of the drape, the drape is collapsible or foldable to form a disposable package containing the fluid to enable hygienic disposal of the drape and the fluid after use of the drape.

Preferably the sheet has a sheet portion between the hole and the edge of the hood which forms a run off for the fluid from the hole to the repository.

Preferably the hood is connected to the sheet at the second end by a fold line so that the sheet and the hood are formed from a single piece of flexible sheet material.

Preferably the hood has first and second side peripheral edges which are connected to the sheet by a liquid impervious sealing method.

Preferably the hood is connected to the sheet by adhesive or heat welding.

Preferably the drape further comprises a closure for closing the repository after use of the drape so as to provide a substantially leak proof repository containing the fluid for disposal.

Preferably the closure comprises a plurality of ribbon ties.

Preferably the closure comprises a draw cord.

BRIEF DESCRIPTION OF THE DRAWINGS

A preferred embodiment of the invention will be described, by way of example, with reference to the accompanying drawings, in which.

DETAILED DESCRIPTION OF THE PREFERRED EMBODIMENT

Figure 1:
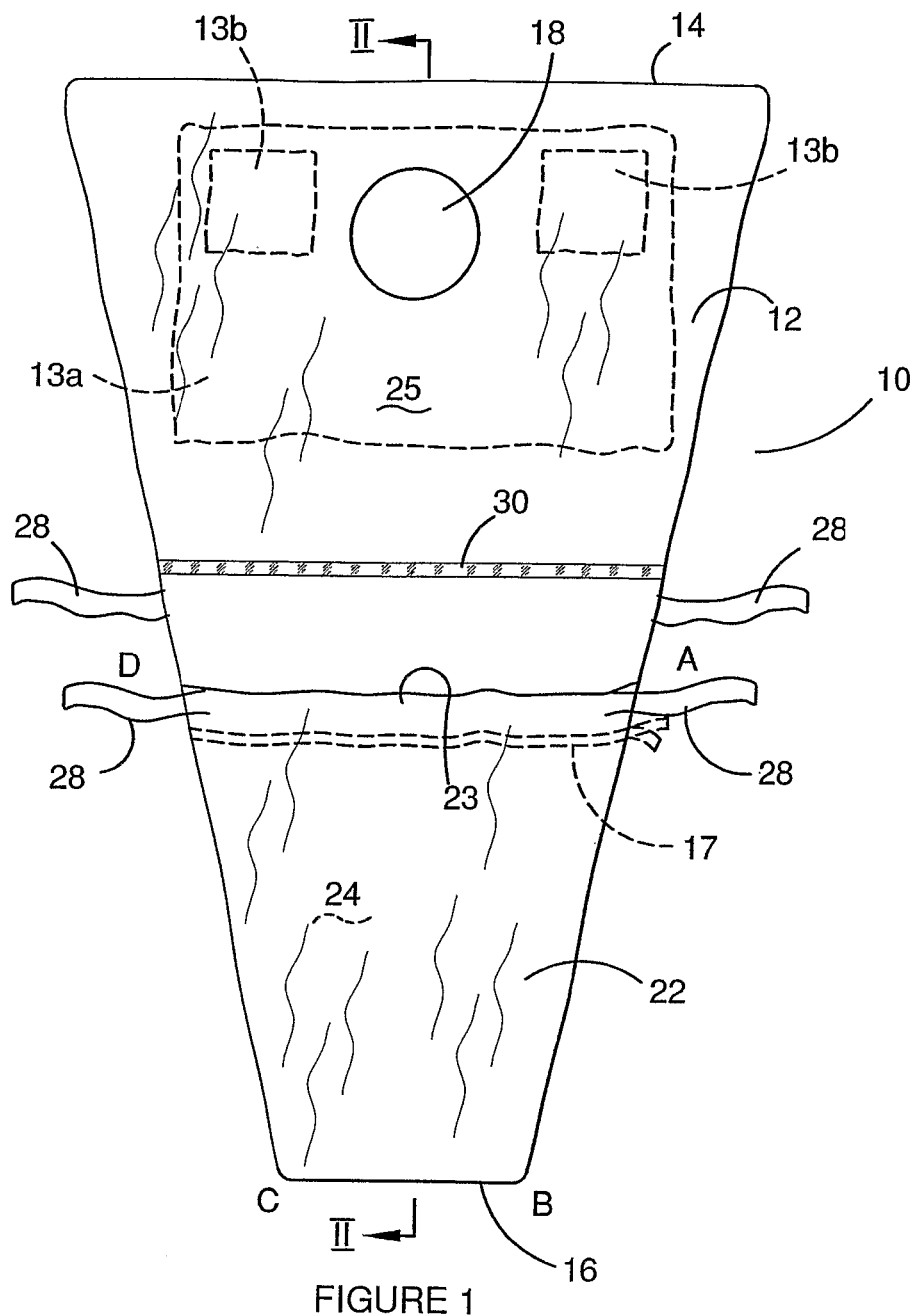
FIG. 1 is a plan view of a urology drape according to one embodiment of the invention.
Figure 2:
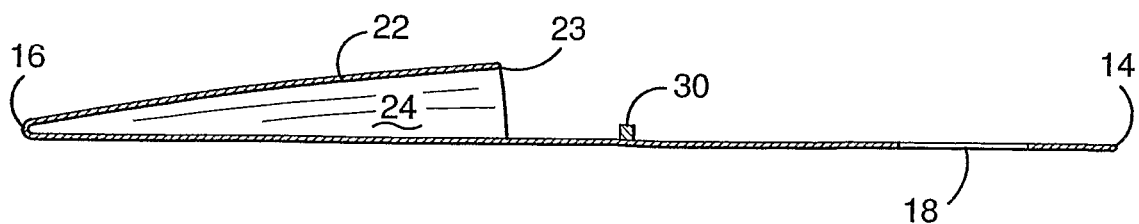
FIG. 2 is a cross-sectional view of the drape of FIG. 1, along the line II-II of FIG. 1.
Figure 3:
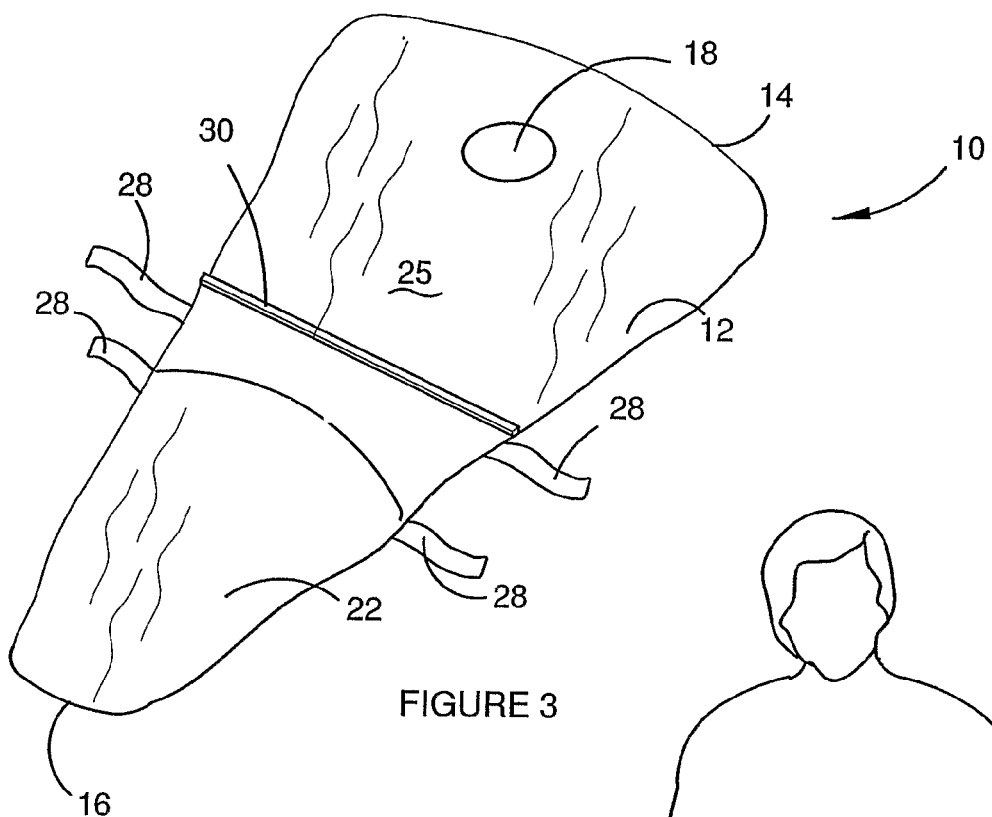
FIG. 3 is a perspective view of the drape of Figure

With references to FIGS. 1 and 2, a urology drape 10 is shown which comprises a flexible sheet 12 which has a first end 14 and a second end 16. The first end 14 is wider than the second end 16 so that the sheet 12 tapers from the from the first end 14 to the second end 16. The sheet 12 is provided with a hole 18 at a first intermediate location between ends 14 and 16 for exposing a patient's genital region when the patient is dressed with the drape 10.

The drape 10 has a flexible hood 22 which overlies the sheet 12 and is attached to the periphery of the sheet 12 from point A to point B to point C and to point D. The points A and D are about halfway along the length of the sheet 12 between the top 14 and bottom 16. The hood 22 is open at its inner end 23 which locates at a second intermediate position between the end 16 and hole 18 so that a repository 24 is defined between the hood 22 and the sheet 12. The inner end 23 forms an edge of the hood which faces the hole 18. The sheet 12 has a sheet portion 25 between hole 18 and end 23 which forms a run-off for fluid from hole 18 to repository 24.

The sheet 12 and hood 22 can be formed from a single piece of material and the hood formed by folding the single piece of material between the points C and B. In such an embodiment, the hood 22 need only be secured to the sheet 12 between the points A and B and the points C and D. Preferably the hood 22 is secured to the sheet 12 by adhesive, heat welding, or any other suitable water impervious sealing method.

The drape 10 is provided with ribbon ties 28 arranged at about the mid-point of the sheet 12 and on hood 22 and which extend outwardly of the sheet 12 and hood 22. In the embodiment shown in the drawings, the ties 28 are in the form of strips of material. However, in other embodiments, the closure may be in the form of a draw cord 17. The draw cord 17 may locate in loops (not shown) or in a sleeve (not shown) which surrounds the drape so that when the draw cord 17 is pulled, the top of the repository 24 adjacent the end 23 is pulled tight. The nature of the ribbon ties 28 or draw string 17 is preferably such that when closing the repository 24, the repository is substantially leak proof so that liquid will not drain out of the collapsed package formed by the drape 10 and the contents of the repository 24, if the package is inverted.

The sheet 12 may be provided with adhesive layers on its rear surface, such as one large layer 13*a* or two smaller layers 13*b* which are covered with a peel-off backing (not shown). The adhesive layers 13*a* or 13*b* serve to attach the drape to a patient to hold the drape on the patient.

A dam 30 can be provided on the sheet 12 between the intermediate end 23 of the hood 22 and the hole 18. Preferably the sheet 12 and hood 22 are formed from liquid proof material such as plastic material. However, the sheet 12 may be provided with an absorbent layer for absorbing bodily fluids discharged during the course of a urology procedure. Thus, bodily fluids can initially be absorbed by the drape and once the drape has absorbed all of the liquid possible, any additional liquid which is discharged can flow along the drape 10 into-the repository 24 and be collected in the repository 24. The dam 30 enables liquid to flow over the dam 30 but will prevent liquid from flowing backwards from the repository 24 towards the opening 18 and end 14 of the drape 10.

Figure 4:
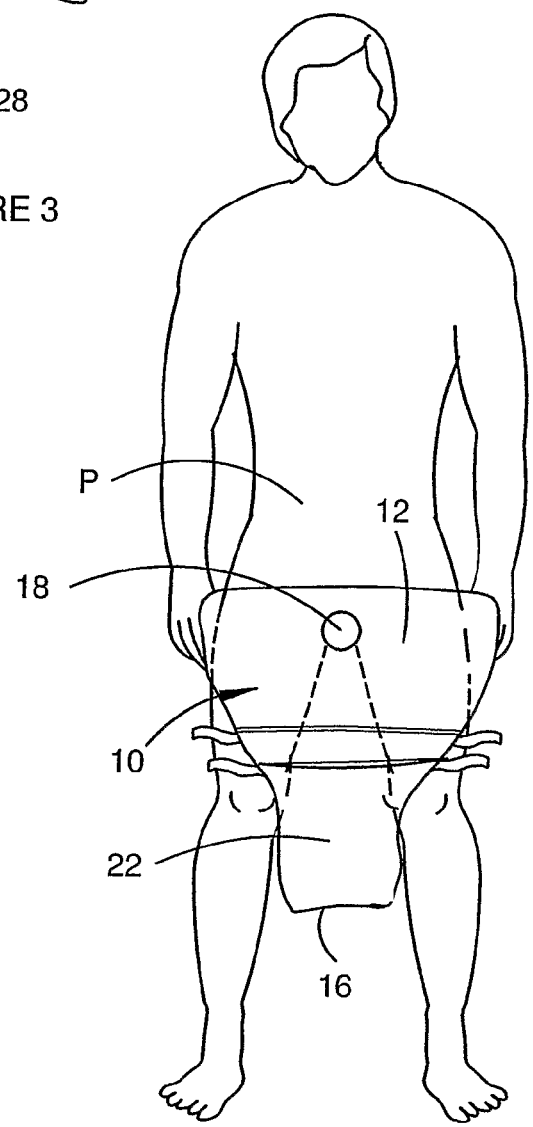
FIG. 4 is a diagram showing the drape in use.

With reference to FIG. 4, a patient P is positioned for a urology procedure by lying on a bed. A towel which may either be a linen towel or a disposable towel is located beneath the patient. The bed on which the patient lies is tilted at an angle of about 5°, in instances where this is not detrimental to the patient, so that liquid will tend to flow down the drape 10 from the hole 18 towards the repository 24 and over the dam 30. The drape 10 can be provided in a sterile package with containers for skin preparation and for washout solution if required, together with gauze, plastic forceps and also possibly gloves and additional towels. The skin of the patient's genitals and grown region is prepared in the conventional manner. The urology drape 12 is then laid over the patient with the narrow end extending down generally between the patient's legs. A non-toxic adhesive may also be provided in the sterile package and may be used to keep the drape 10 in place on the patient during the procedure. The urology procedure is then performed, which may be the insertion or replacement of a catheter, washout, cystoscopy procedure or any other genital procedure requiring a sterile field. In the case of the insertion or replacement of a catheter, the catheter is inserted with a catheter directed towards the repository 24. When urine flows, it is therefore able to be caught in the repository 24 or flow down the drape 12 into the repository 24 over the dam 30.

If a washout is required, the washout is performed and the liquid, when returned, is easily squirted into the repository 24.

A urinary catheter drainage bag may then be connected to the urinary catheter and a washout or spigot connected if required.

Any soiled goods such as gauze, cotton wool, plastic forceps, gloves or the like, may be placed in the repository 24 once the procedure is finished, as this section is away from the operative field and need not necessarily remain sterile.

Figure 9:
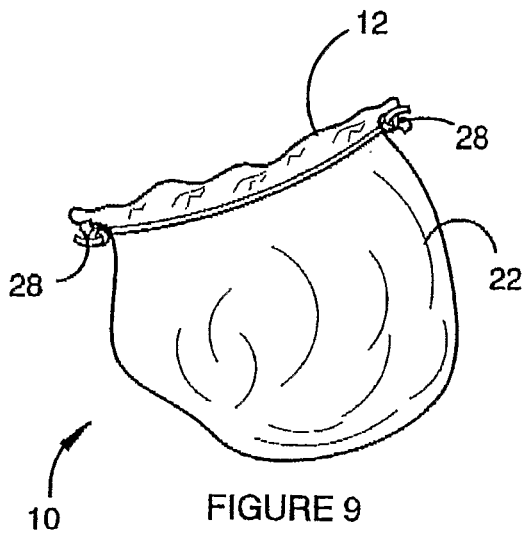
FIGS. 9 and 10 are views showing a used drape in a folded or collapsed condition for disposal.
Figure 10:
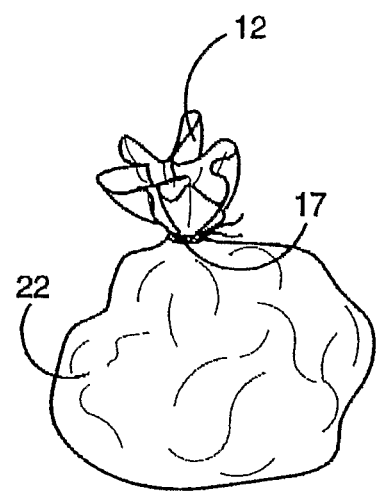

When the procedure is finished, the drape 10 is removed from the patient and the top part of the sheet 12 between the hood 22 and the end 14 is folded onto itself and inserted into the repository 24 to place the drape in a folded or collapsed condition (FIGS. 9 and 10). The ribbon ties 28 can then be used to tie off the repository 24, or the repository can be closed by pulling draw cord 17 tight, to close the repository 24 with all the contaminated waste, including urine, blood and used articles. The tied drape can then be placed in an infectious diseases disposal unit.

In the preferred embodiment of the invention the sheet 12 is a single sheet of material. However, in other embodiments, the repository 24 could be formed as a pouch with one surface of the pouch being connected to a sheet so that the surface of the pouch and the sheet form the entire sheet and the other surface of the pouch forming the hood.

In one embodiment the drape 10 has a width at end 14 of about 90 cm, a length of about 110 cm and a hole 18 has a circumference of about 10 cm. The dam 30 extends across the entire width of the approximate midpoint of the drape 10 which may have a width of 75 cm and may have a height of up to 5 cm.

Figure 5:
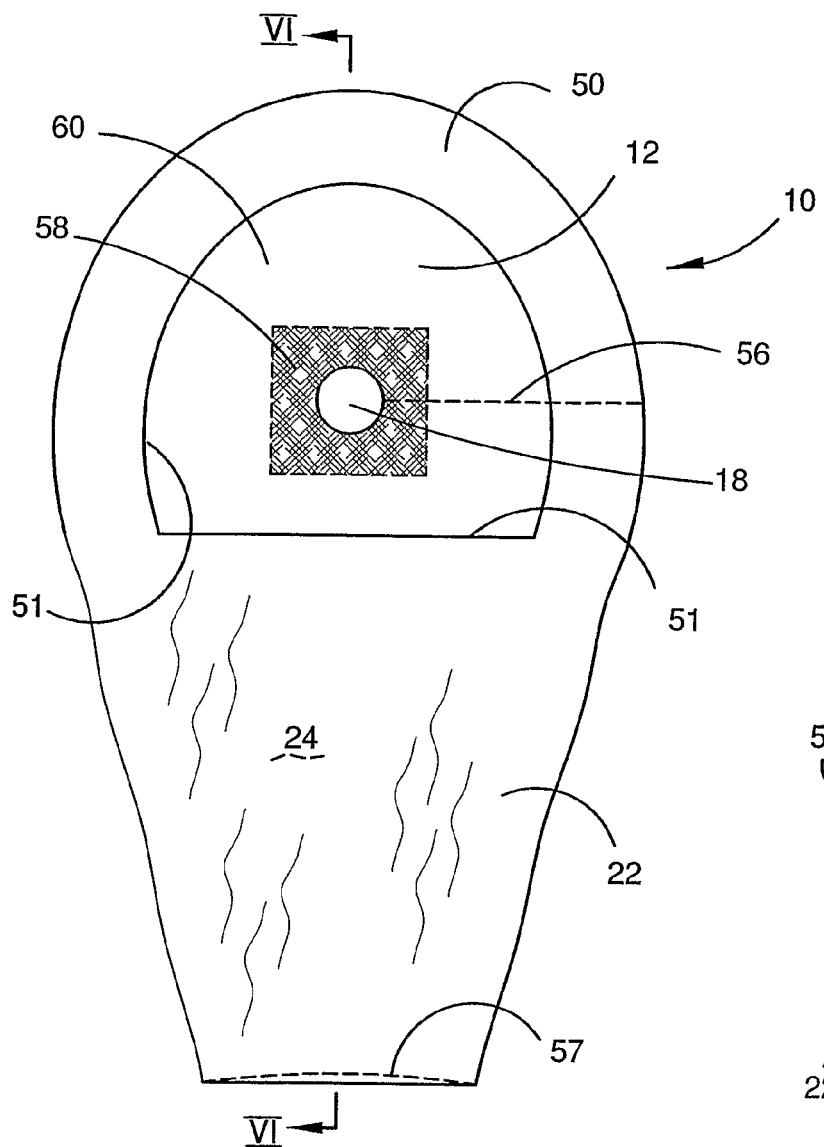
FIG. 5 is a plan view of another embodiment of the invention.
Figure 6:
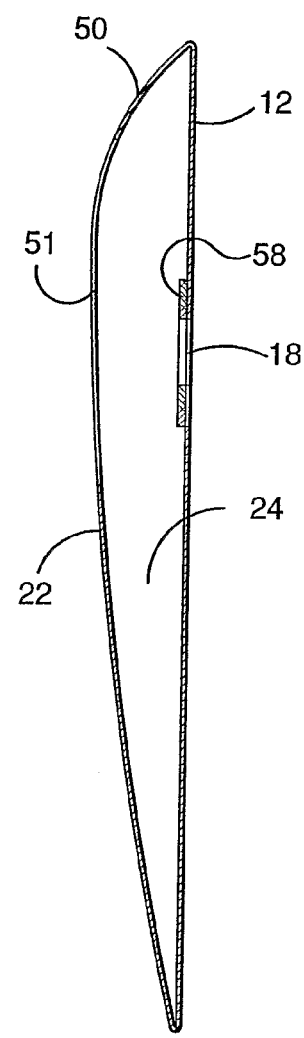
FIG. 6 is a cross-sectional view along the line VI-VI of FIG. 5.

FIGS. 5 and 6 show a further embodiment of the invention in which like reference numerals indicate like parts to those previously described.

In this embodiment the sheet 12 above the hood 22 is provided with a wall 50 which is a continuation of the hood 22 about the periphery of the sheet 12 above the hood 22. Thus, the hood 22 and the wall 50 effectively define a dam around the region of the drape above the hood 22 for catching any liquid which spills onto the drape and does not flow immediately down in the repository 24.

The inner periphery 51 of the wall 50 and the top 53 of the hood 22 (about where the dam 30, not shown, is located) define a working area 60 which is surrounded by the hood 22 and wall 50 for catching any liquid which is discharged from the patient.

The drape 10 may also have a perforation 56 extending from the hole 18 to the periphery of the sheet 12 to allow easy tear-away of the drape from a patient so a catheter (not shown) is not disturbed when the drape is removed. The repository 24 may also have a perforation 57 at its bottom for allowing easy drainage of fluids, or a tap or the like can be connectable to the drape at the bottom of the repository 24.

An absorbent pad of material 58 may also surround the hole 18 for absorbing fluid immediately around the opening 18.

Figure 7:
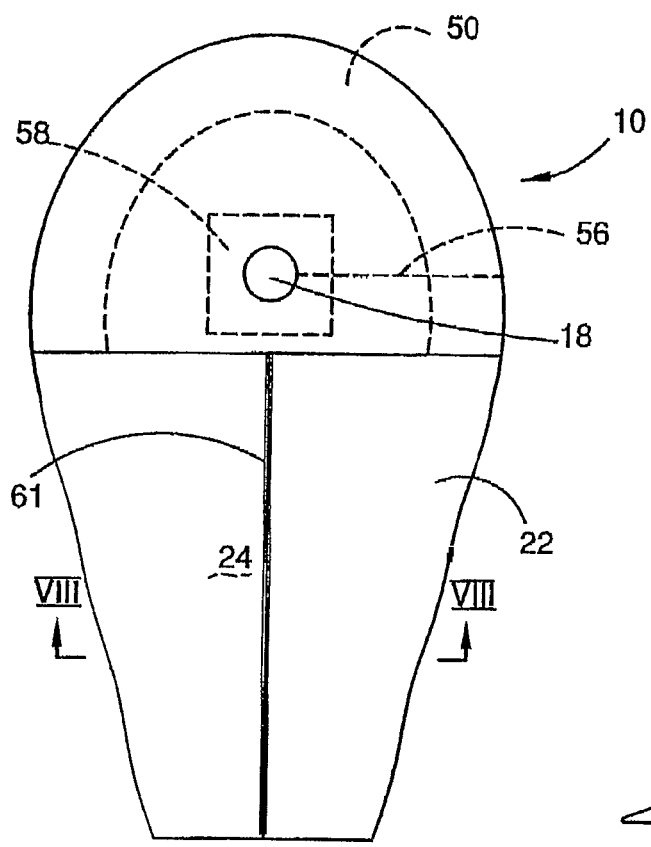
FIG. 7 is a plan view of a still further embodiment of the invention.
Figure 8:
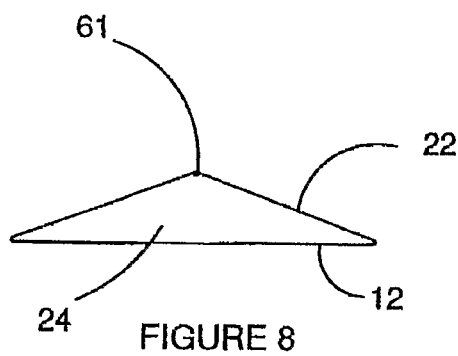
FIG. 8 is a cross-sectional view along the line VIII-VIII of FIG. 7.

FIGS. 7 and 8 show a still further embodiment which may have all of the features described with reference to FIGS. 5 and 6. In this embodiment the hood 22 is provided with a stiffened fold line 61 so that the hood 22 takes up an inverted V-shape, as best shown in FIG. 8. This assists in opening the repository 24 for the collection of fluid. The fold 61 or the hood 22 may also include reinforcing material for holding the hood-22 in the configuration shown in FIG. 8.

The drape 10 may be of V-shape, as shown in FIG. 1, square shape, or triangular with the hood 22 ending in a pointed apex rather than a flat base. The working region may be generally square or rectangular, as shown in FIG. 1, or part circular, as shown in FIG. 5.

The urology drape 10 may be used for other procedures than urology procedures if required by appropriate location of the drape to part of a person's body to expose the procedure area of the body through the hole 18.

Since modifications within the spirit and scope of the invention may readily be effected by persons skilled within the art, it is to be understood that this invention is not limited to the particular embodiment described by way of example hereinabove.

In the claims which follow and in the preceding description of the invention, except where the context requires otherwise due to express language or necessary implication, the word "comprise", or variations such as "comprises" or "comprising", is used in an inclusive sense, i.e. to specify the presence of the stated features but not to preclude the presence or addition of further features in various embodiments of the invention.

The invention claimed is:

1. A method of performing a urology procedure, comprising:
   dressing a patient with a drape having:
      a flexible sheet for location on a patient between a patient's legs when the patient is in a supine position, the flexible sheet having a first end and a second end;
      a hole in the flexible sheet at a first intermediate location between the first and second ends;
      the flexible sheet having a second intermediate location between the hole and the second end, and a first portion extending between the first end and the second intermediate location, and a second portion extending between the second intermediate location and the second end, said hole being formed in said first portion;
      a flexible hood overlaying the second portion of the sheet and extending between the second end of the sheet and the second intermediate location;

the hood having a periphery and being connected to the sheet about the periphery of the hood except for an edge of the hood facing the hole;

the second portion of the sheet and the hood forming a flexible repository therebetween for catching and retaining bodily fluids;

the drape including a closure for closing the repository at said second intermediate location so as to provide a substantially leak proof repository;

performing the urology procedure so that bodily fluids discharged as a result of the procedure collect in the repository;

removing the drape from the patient; and collapsing or folding the drape by locating the first portion together with said hole in the repository and closing the repository, with the first portion and the hole therein, with the closure to form a disposable package containing the fluid to enable hygienic disposal of the drape and the fluid after use of the drape.

2. The method of claim 1, wherein the method further comprises tilting the patient to facilitate flow of discharged liquid down into the repository.

3. A urology drape comprising:

a flexible sheet for location on a patient between a patient's legs when the patient is in a supine position, the flexible sheet having a first end and a second end;

a hole in the flexible sheet at a first intermediate location between the first and second ends;

the flexible sheet having:
 a second intermediate location between the hole and the second end,
 a first portion extending between the first end and the second intermediate location, said hole being formed in said first portion; and
 a second portion extending between the second intermediate location and the second end;

a flexible hood overlaying the second portion of the sheet and extending between the second end of the sheet and the second intermediate location;

the hood having a periphery and being connected to the sheet about the periphery of the hood except for an edge of the hood facing the hole;

the second portion of the sheet and the hood forming a flexible repository therebetween for catching and retaining bodily fluids;

the drape including a closure for closing the repository at said second intermediate location so as to provide a substantially leak proof repository;

whereby after use of the drape, the drape is collapsible or foldable by locating the first portion together with said hole in the repository and closing the repository, with the first portion and the hole therein, with the closure to form a disposable package containing the fluid to enable hygienic disposal of the drape and the fluid after use of the drape.

4. The drape of claim 3, wherein the sheet has a sheet portion between the hole and the edge of the hood which forms a run off for the fluid from the hole to the repository.

5. The drape of claim 3, wherein the hood is connected to the sheet at the second end by a fold line so that the sheet and the hood are formed from a single piece of flexible sheet material.

6. The drape of claim 3, wherein the hood has first and second side peripheral edges which are connected to the sheet by a liquid impervious sealing method.

7. The drape of claim 3 wherein the hood is connected to the sheet by adhesive or heat welding.

8. The drape of claim 3, wherein the closure comprises a plurality of ribbon ties.

9. The drape of claim 3, wherein the closure comprises a draw cord.

10. The drape of claim 3, wherein the second intermediate location is about halfway between the first end and the second end.

11. The drape of claim 3, wherein the length between the first end and the second end of the flexible sheet is about 110 cm.

12. The drape of claim 3, wherein the first end of the sheet is wider than the second end so the drape tapers from the first end to the second end.

13. The drape of claim 3, wherein a dam is provided between the hole and the hood so as to prevent backflow of fluid captured in the repository towards the first end of the sheet.

14. The drape of claim 3, wherein the drape has a wall extending about a periphery of the sheet between the first end and the hood.

15. The drape of claim 14, wherein the wall is integral and forms a continuation of the hood, and a work area is defined between the hood and the wall.

16. The drape of claim 15, wherein the hole is provided in the work area.

17. The drape of claim 16, wherein the hole is surrounded by an absorbent pad.

18. The drape of claim 15, wherein a perforation extends from the hole to a periphery of the drape for facilitating tearing of the drape to remove the drape from a patient.

19. The drape of claim 15, wherein the hood takes up a generally inverted V-shape configuration.

20. The drape of claim 19, wherein the hood includes a fold line for forming the inverted V-shape configuration.

* * * * *